United States Patent [19]

Goldner

[11] 4,032,856

[45] June 28, 1977

[54] DRIFT COMPENSATED AMPLIFIER, PARTICULARLY FOR MEASURING SIGNALS

[75] Inventor: Heinz-Dieter Goldner, Schwalbach, Taunus, Germany

[73] Assignee: Hartmann & Braun Aktiengesellschaft, Frankfurt am Main, Germany

[22] Filed: Nov. 10, 1975

[21] Appl. No.: 630,335

[30] Foreign Application Priority Data

Nov. 13, 1974 Germany ............................ 2453720

[52] U.S. Cl. ...................................... 330/69; 73/23; 330/9; 330/30 D; 330/86
[51] Int. Cl.² .......................................... H03F 3/45
[58] Field of Search ................. 73/23, 23.1; 330/9, 330/30 D, 69, 86

[56] References Cited

UNITED STATES PATENTS

| 3,441,863 | 4/1969 | Moriyasu | 330/9 |
| 3,504,521 | 4/1970 | Luckers | 330/9 X |

Primary Examiner—Rudolph V. Rolinec
Assistant Examiner—Lawrence J. Dahl
Attorney, Agent, or Firm—Ralf H. Siegemund

[57] ABSTRACT

A gas analyzer has an output amplifier circuit which is drift compensated in that zero volts are established across a gain network for a particular low point measuring signal as the amplifier provides an output on the basis of a particular bias, while the gain network is adjusted so that the amplifier output equals a second reference signal. The drift compensation is automated in that the bias and the reference are used to drive adjusting devices while the gas analyzer receives particular reference gases.

13 Claims, 2 Drawing Figures

DRIFT COMPENSATED AMPLIFIER, PARTICULARLY FOR MEASURING SIGNALS

BACKGROUND OF THE INVENTION

The present invention relates to drift compensation of measuring instruments, and more particularly the invention relates to drift compensation in the circuit that processes the signals provided by an analyzer, such as a gas analyzer.

The German printed patent application 1,965,804 describes a gas analyzer with measuring signal amplifier wherein a program device causes reference gases to be provided to the gas analyzer for establishing therein particular measuring states resulting in particular output signals of the amplifier, which are then varied to agree with reference signals for these specific measuring states. The variation involves variation of resistance devices. This kind of adjustment as carried out by the known apparatus yields correct drift compensation only if one of the reference gases is such that the analyzer output is to represent an exact zero condition of whatever component it is looking for normally. This, however, is a considerable constraint. If, for any reason, such zero point adjustment is not possible, then the result of the adjustment in one instance is, in fact, altered by the subsequent adjustment for the other reference gas. The correction, therefore, must be repeated, possibly several times, and the equipment alternates back and forth between the two reference gases and measuring states to obtain a stepwise approximation process of adjustment.

DESCRIPTION OF THE INVENTION

It is an object of the present invention to provide a drift compensated and compensatable amplifier in which two definite inputs, such as measuring signals representing definite states and known quantities can be used to establish the transfer characteristics of the amplifier, whereby none of these states needs to represent an exact zero condition for the measuring range.

It is a specific object of the present invention to provide for automatic drift compensation in measuring amplifiers which permits automated establishing of specific measuring states followed by automated trimming and adjusting procedure, whereby specifically a subsequent trimming and adjusting does not alter the effect of a preceding one.

In accordance with preferred embodiment of the invention, it is suggested to provide a measuring signal amplifier with input and output circuit, each including adjustable means and to connect a particular source for biasing potential permanently to the amplifier to be included in the formation of the output signal by the amplifier. The adjustable means in the input circuit is adjusted so that for a first reference condition in the formation of the measuring signal the output of the amplifier is established with zero volts across the adjustable means in the output circuit whereby the then prevailing measuring signal as applied together with the biasing source establishes the output. The adjustable means in the output circuit are adjusted in accordance with the second reference condition in the formation of the measuring signal.

The amplifier circuit may be constructed as a device, which has one or several stages, whereby the output circuit of the one or of the lowest stage (e.g. one of the higher stages) includes gain factor determining resistances. The bias as applied causes a zero voltage drop across the gain adjusting resistor for properly trimmed input circuit upon establishing a particular condition for the measuring device. The gain is adjusted subsequently in accordance with a second particular condition for the measuring device. The biasing means being a permanent part of the amplifier may be connected to the input circuit of the single stage or in the output circuit of the lowest stage.

If applied to gas analysis, two different reference gases are used to establish the two reference conditions in the gas analyzer corresponding to particular output signals of the analyzer which are used to drive the amplifier and to adjust the amplifier to particular set points in the output. The reference gases may be provided for low and high values for the particular gas component to be detected, whereby, however, the low point may but does not have to be an exact zero point.

The invention permits utilization of the known automated drift compensation with added advantage that back and forth trimming is not needed. Instead, an electrical reference signal corresponding to the set points to be obtained when the measuring signals represents one or the other of the specific conditions, is used to be compared with the output of the amplifier and one or the other of the adjustable elements is adjusted. It is a specific feature of the invention that one of the reference signals used here is the biasing source that is part of the permanently used circuitry in the amplifier.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawing in which:

Proceeding now to the detailed description of the drawing, FIG. 1 shows a gas analyzer G receiving gas for analysis via a conduit L and providing an electrical output signal to two output lines. The specific example of FIG. 1 shows the two output lines at floating potential, any connection to ground runs through biasing circuitry of the output amplifier to be described shortly. The gas to be analyzed may originate from different sources. A regular source furnishes gas B to be analyzed, e.g. on a running basis. E and N respectively denote reference gases of known consistency to be described later. Two pulse-operated magnetic valves $M_1$ and $M_2$ are controlled to connect but one source for gas at a time to the input conduit of the analyzer G.

Figure 1:
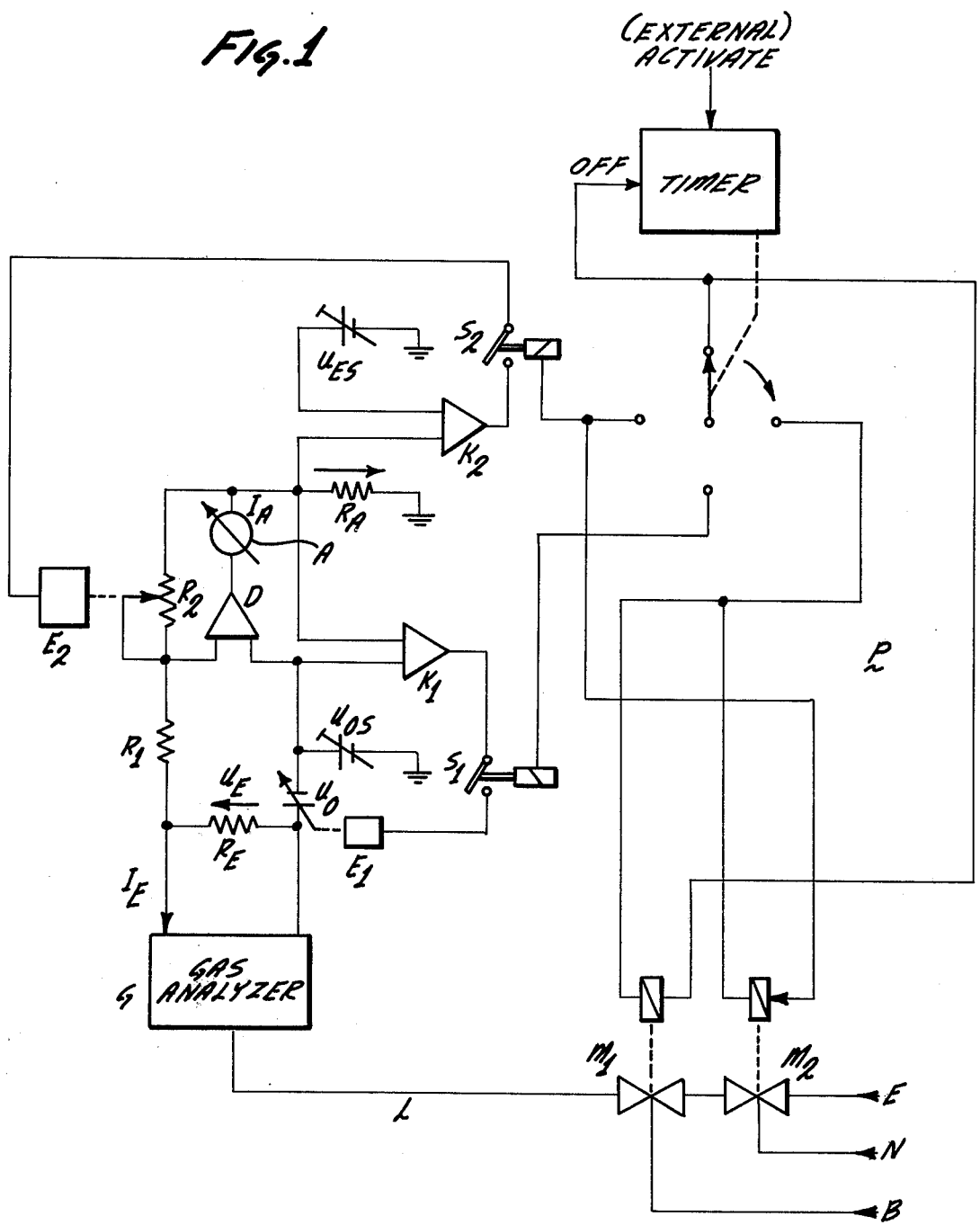
FIG. 1 is a circuit and block diagram of an example of the preferred embodiment of the invention.

The principal electrical component for processing the measuring signal derivable from analyzer G is a differential amplifier D connected to the two output lines of device G. The latter two output lines are interconnected by a resistor $R_E$ serving as one of the input resistors for amplifier D. The main signal path from analyzer G runs through another input resistor $R_1$ to one of the input terminals of amplifier D. The other input terminal of the amplifier is connected to the second output line of analyzer G via an adjustable voltage source $U_o$.

The differential amplifier D drives an indicating instrument A and the current is, in parts, fed back via a resistor $R_2$ to the first input of the ampplifier to obtain negative feedback. Thus, the amplifier D functions as operational amplifier whose gain is determined by the ratio of the resistors $R_1$ and $R_2$ and establishing a current node at the signal input terminal of amplifier D. The resistor $R_2$ is adjustable rendering the gain of the amplifier adjustable therewith.

A portion of the output current flows through an output resistor $R_A$ to ground and is proportional to the input current $I_E$ of the analyzer. The voltage drop $U_A$ across resistor $R_A$ is, therefore, indicative of the gas component in the gas being analyzed. The entire output current flows through an indicating instrument A.

Aside from the variable voltage source $U_o$, the reference branch of the input circuit of amplifier D includes an ajustable but operationally constant voltage source $U_{os}$ connected between that second input terminal of amplifier D and ground, and serving as reference for a low level or low point reference measurement. The circuit includes a second reference source $U_{ES}$ for a high point reference measurement which, however, is not a permanently effective component in the amplifier as far as signal amplification is concerned.

The circuit includes two comparators $K_1$ and $K_2$; Comparator $K_1$ receives as inputs the voltage $U_A$ and the voltage $U_{os}$. Comparator $K_2$ receives as inputs $U_A$ and $U_{ES}$. The two comparators respectively provide their outputs to drive circuits $E_1$ and $E_2$. The drive circuit $E_1$ adjusts the voltage source $U_o$, and the drive circuit $E_2$ adjusts the variable resistor $R_2$.

The devices E can be electro-magnetic adjusting devices with small servo-motors and possibly, driver amplifiers which are being controlled from the respective comparator. One may also use a circuit as shown in German printed patent application 1,965,804 showing resistance adjustment by means of counters and transistor switches, which places fixed resistors in and out of circuit.

The comparators and drive circuits operate in separate loops to provide for adjustment of parameters that may need adjustment. These adjusting loops are not effective simultaneously but sequentially through closing of relay switches $S_1$ and $S_2$.

The device is under control of a program control apparatus P which normally holds the device in an operational state in which measuring gas B is passed to the analyzer, and both switches $S_1$, $S_2$ are open so that regular measurement takes place. Whenever drift compensation is deemed necessary, device P sets into motion a sequence of operations which, in the essence, are merely a plurality of timed switching operations carried out in a particular sequence. The program control may, for example, be just a step switch closing one contact at a time for a specified duration until a timer moves the step switch to the next position. The step switch may operate in rotary fashion (or, more generally, in a ring) to run through one sequence of compensation control and to return to the normal operating state and the timer which advances the step switch is deactivated. The timer must be started anew from the outside for another drift compensation.

As stated, the normal state of operation has the magnetic valves in a position in which gas B is fed to the analyzer and switches $S_1$ and $S_2$ are open, so that the drives $E_1$, and $E_2$ necessarily maintain their position. If drift compensation is desired device P activated and moves to the first step. Accordingly, valve $M_1$ is changed in position to cut off the source for gas B, and valve $M_2$ is placed in a position so that a first reference gas N is passed to the analyzer. Actually, a venting phase may precede this step, but the reference gas may be used also to flush any remainder of gas B out of the analyzer. After a settling period the timer of device P moves to the next step in which the valves $M_1$, and $M_2$ will retain their position but contact $S_1$ is closed.

The first reference gas N has a specific consistency corresponding to a low point in the measurement. For example, it may consist of pure host gas with zero concentration of the particular component which is normally included in gas B and measured by the device. The reference gas N may, however, contain a low concentration of the gas to be measured. Generally speaking, gas N is to have a definite consistency resulting in an output near the low end of the scale.

The circuit will produce a particular output $U_A$ which is compared in comparator $K_1$ with $U_{OS}$. If there is a difference, device $E_1$ is actuated by the non-zero comparator output to adjust (trim) the voltage source $U_O$ until the resulting output signal $U_A$ agrees with $U_{OS}$.

Conceivably, neither flushing nor even a settling period may be needed prior to causing the adjusting to work. Actually, it may be desirable to close the switch $S_1$ and to cause the system $K_1 - E_1$ to respond immediately as the reference gas N becomes effective, rather slowly at first. This gradual build up has the effect that due to the adjustment of device $E_1$, voltage source $U_O$ is at first moved out of its previous position thereby introducing a large error from which the adjustment is then homed-in as reference gas N prevails in the analyzer. This mode of operation may overcome any sluggishness of response, if the needed drift compensation is actually only a minor one.

As far as the amplifier circuit is concerned, a condition $U_A = U_{OS}$ is established when $U_O$ is adjusted to equal the particular $U_E$ as produced by the analyzer for gas N. $U_O = U_E$ and $U_A = U_{OS}$ produces a potential at least approximately equal to $U_{OS}$ at both input terminals of amplifier D. In other words, the input circuit for amplifier D as adjusted transforms the measuring signal as representing the reference gas N to equal the bias as effective on the reference terminal of amplifier D. On the other hand, zero voltage is established across the two gain resistors, $R_1$ and $R_2$, because the differential voltage in the input of amplifier D is negligible.

It follows, therefore, that for the particular reference gas N the input circuit of amplifier D is adjusted for current feed-back and reproducible output commensurable with the permanent reference and bias $U_{OS}$. It is significant that this operational state can be and is maintained independently from any variation in resistor $R_2$. Thus, this resistor can be freely adjusted without changing the adjustment of the low set point in the indication.

As the device can expect that this adjustment is completed in a specific amount of time, the timer in program device P may readily shift the program switch to the next step. The next step causes a change in the state of the valve $M_2$ to disconnect the analyzer G from the source of reference gas N and connects line L to the source of reference gas E. Gas E is characterized by a specific concentration of the measuring component, e.g. the expected maximum.

Also in the next step, switch $S_1$ is opened to arrest device $E_1$ in position so that the voltage source $U_O$ remains now as adjusted. Switch $S_2$ is closed thereafter, possibly with a slight delay as far as opening of switch $S_1$ is concerned ensuring high point adjustment does not disturb the adjusted low point. Opening of switch $S_1$ should actually precede all other changes in the system at this point, which is inherently the case if the response delay for magnetic valve $M_2$ is larger than the drop off delay of switch $S_1$.

As switch $S_2$ is closed, comparator $K_2$ becomes effective. That comparator compares the now present output signal $U_A$ with the reference signal $U_{ES}$ and if there is a disagreement, drive $E_2$ is actuated and readjusts the gain of amplifier D in that drive $E_2$ and trims resistor $R_2$ until $U_A$ equals $U_{ES}$. This adjustment procedure can be expected to be completed within a particular period of time, whereupon program device P opens switch $S_2$ and causes subsequently valve $M_1$ to disconnect the source for reference gas E from the analyzer while restoring the connection to receive gas B. This last step may also deactivate the timer of the step switching device to maintain that regular state until an external demand is made to readjust the equipment.

The relationship between input $U_E$ and output $U_A$ can be written as $$U_A = U_{os} + (U_E - U_o) \cdot (R_2/R_1)$$

wherein $R_2/R_1$ is the gain K of the amplifier D. The low point adjustment as described establishes directly $U_E = U_O$ resulting in $U_A = U_{OS}$. In other words, the adjustment of $U_O$ by operation of comparator $K_1$ and drive $E_1$ causes $U_E - U_O$ to drop to zero, so that the low point measuring signal $U_E$ renders the output independent from the gain K. The high point adjustment establishes $U_A = U_{ES}$, in that for the particular high point measurement $U_E$, the gain factor $K = R_2/R_1$ is adjusted accordingly.

Figure 2:
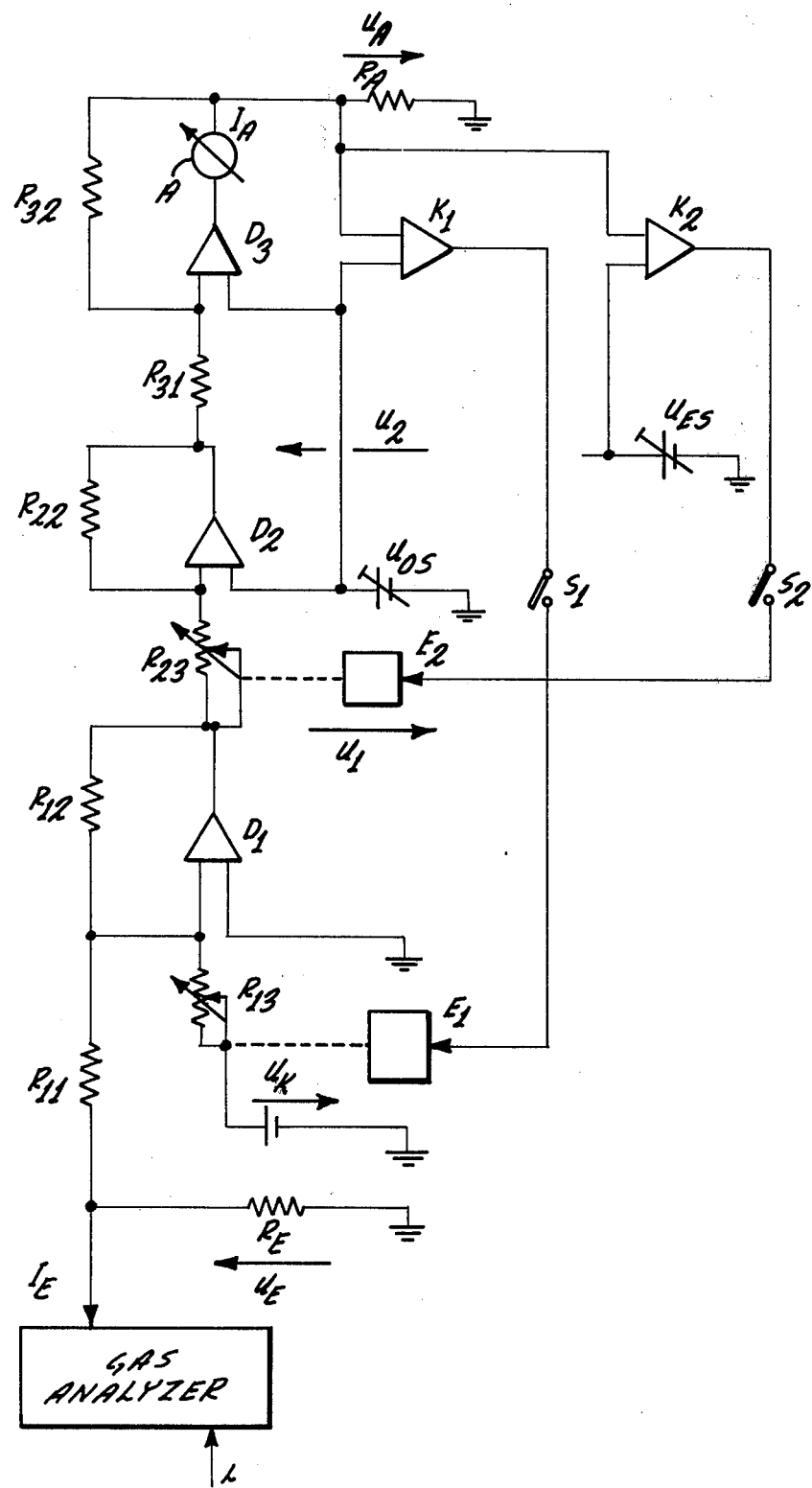
FIG. 2 is a modified diagram in accordance with the best mode of operation.

Turning now to FIG. 2, this figure shows only the electrical part of the modification and the gas analyzer G. The valves, gas sources and program device are all the same as in FIG. 1 and have been omitted from the illustration. The circuit is designed as follows The signal terminal of the gas analyzer is connected to the signal input terminal of a differential amplifier $D_1$ via a resistor $R_{11}$. $R_E$ is again the shunt resistor across the output terminals of the analyzer, but the reference terminals of the gas analyzer and of the differential amplifier $D_1$ are grounded. The feed-back resistor is denoted $R_{12}$ and is not adjustable. The signal input terminal of amplifier $D_1$ is further connected via an adjustable resistor $R_{13}$ to a source of reference potential $U_K$. The resistor $R_{13}$ is adjustable in this instance by drive $E_1$ to provide for the low point trimming.

The output of differential amplifier $D_1$ is fed to the signal input of a second differential amplifier $D_2$, via an adjustable resistor $R_{23}$ which is operable by the second drive $E_2$ for the high point adjustment. Amplifier $D_1$ can be considered to be a part of an input circuit for amplifier $D_2$ while $R_{23}$ can, on the one hand, be regarded as coupling resistor for the two amplifiers, but $R_{23}$ can also be regarded as part of the gain circuit for amplifier $D_2$.

The reference input for amplifier $D_2$ is connected to the source of reference voltage $U_{OS}$ as well as to one input of the comparator $K_1$. $R_{22}$ denotes the feed-back resistor of differential amplifier $D_2$. The output of differential amplifier $D_2$ is fed via a resistor $R_{31}$ to a third differential amplifier $D_3$, which is the instrument driver, feeding its output to instrument A. The reference source $U_{OS}$ is also connected to differential amplifier $D_3$, and the output of the latter includes the output resistor $R_A$ as well as a connection to one input terminal each of the two comparators $K_1$ and $K_2$; the latter has its second input connected to the source for the high point reference voltage $U_{ES}$.

The low point adjustment is carried out as follows: Switch $S_1$ is closed and comparator $K_1$ again compares the resulting output $U_A$ with the reference $U_{OS}$. The driver $E_1$ adjusts the resistor $R_{13}$ through which current from bias source $U_K$ is fed to the signal input node of amplifier $D_1$. The amplifier $D_1$ stabilizes for zero current in the signal input node and ground potential at that terminal so that a particular voltage $U_1$ is established by operation of the feedback and by the gain of the amplifier $D_1$. That output voltage $U_1$ is equal to $U_A = U_{OS}$ for the following reason The adjustment of $R_{13}$ stops when $U_A = U_{OS}$ as that causes the comparator $K_1$ to produce zero output. When $U_A = U_{OS}$ zero current in the signal input node of differential amplifier $D_1$ requires zero voltage drop across resistors $R_{31}$ and $R_{32}$, because both input terminals of $D_3$ will have the potential of $U_{OS}$. Thus, the output voltage $U_2$ of amplifier $D_2$ is also $U_{OS}$, which in turn means that no current flows through resistors $R_{22}$, $R_{23}$. Thus, the output $U_1$ of amplifier $D_1$ is also equal to $U_{OS}$. In other words, the measuring signal is also here transformed by adjustment to be equal to the bias for differential amplifier $D_2$. Decisive is that variable resistor $R_{23}$ may have any value, and any subsequent adjustment thereof will not alter the low point adjustment as it affects the output of instrument driver $D_3$.

For adjustment of the high point, the gas analyzer is controlled as outlined above; switch $S_2$ is closed after switch $S_1$ has been opened. The comparator $K_2$ compares the reference voltage $U_{ES}$ with the output voltage $U_A$, and device $E_2$ adjusts the input resistor $R_{23}$ for amplifier $D_2$. Actually, the gain of amplifier $D_2$ is adjusted by this operation until $U_A$ equals $U_{ES}$.

The circuit of FIG. 2 satisfies the following conditions:

$$U_A = U_{os} + (U_E - U_o') \cdot K'$$

wherein $K' = R_{22}/R_{23}$, i.e. the gain of the amplifier $D_2$ $$U_o' = (R_{12}/R_{13}) \cdot U_K + U_{os}$$

For the low point adjustment, the voltage $U'_O$ is adjusted to equal $U_E$. The output voltage $U_A$ for this case is $U_{OS}$; the adjustment involves resistor $R_{12}$. The high point adjustment involves the gain $K'$ of the differential amplifier $D_2$.

Upon completion of adjusting $U_O'$ and $K'$, the equation above is the operational characteristics with which the system processes input signals $U_E$ as generated by the analyzer when testing gas B.

The three stage cascade has particular advantages. For example, one can use similar modules for adjustment of both, high and low points; one module being $D_1$ with $R_{12}$, $R_{13}$ and, possibly, device $E_1$. The other module is $D_2$, $R_{22}$, $R_{23}$ and, possibly, $E_2$. All voltages as they appear, such as $U_E$, $U_A$, but particularly including the auxiliary voltages $U_{OS}'$, $U_{ES}'$, $U_K'$ etc. are referenced to ground which means that one can derive them from a single constant voltage source through suitable taps.

The invention is not limited to the embodiments described above, but all changes and modifications thereof not constituting departures from the spirit and scope of the invention are intended to be included.

I claim:

1. An amplifier circuit for processing measuring signals from a source for measuring signals with built-in drift compensation, comprising:
    a differential amplifier means with resistive gain network in feedback configuration which includes an adjustable resistor, the amplifier means further having an output circuit;
    a first source for non-ground, biasing voltage connected to one of the inputs of the differential amplifier means so that for a voltage similar to the biasing voltage when applied to the other one of the inputs, the gain network has no voltage across, and the output circuit of the amplifier means provides an output equal to said biasing voltage;
    an input circuit connected to the other one of the inputs as well as to the source for the measuring signals and including an adjustable means; a first comparator having its inputs connected to said output circuit and to the first source and including operating means for adjusting said adjustable means in response to a differential across said inputs to cause a first particular measuring signal to be transformed so that the input circuit applies a signal equal to said biasing voltage to said other input of the differential amplifier; a second source for non-ground voltage; and
    a second comparator having its inputs connected to said output circuit and to said second source and including operating means for adjusting said adjustable resistor in response to a differential across the inputs of the second comparator so that a second comparator so that a second particular measuring signal be transformed and the gain network is adjusted until the output as provided by the output circuit equals the voltage of said second source.

2. An amplifier circuit as in claim 1, wherein the input circuit includes another differential amplifier with a gain circuit and an adjustable bias, constituting said adjustable means.

3. An amplifier as in claim 1, wherein the input circuit includes an adjustable voltage source as said adjustable means.

4. An amplifier circuit as in claim 1, wherein said source of measuring signals includes means for generating particular measuring states for calebration purposes to obtain the production of said particular measuring signals.

5. A drift compensated amplifier, comprising:
    an amplifier means with an input circuit connected to receive a measuring signal, further having a gain adjustment circuit;
    an adjustable means in the input circuit for modifying the measuring signal;
    a first and a second comparator, each connected to receive the output of the amplifier means;
    a first and a second reference sources respectively connected to the inputs of the first and second comparators;
    first and second drive means respectively connected for operation by the first and second comparators and further respectively connected to adjust the gain adjustment circuit and the adjustable means; and
    the first reference source being connected further to the amplifier means independently from the gain adjustment circuit, but having its signal combined with the measuring signal as modified by the adjustable means to contribute to the formation of the output and determining the output when the first drive means has adjusted the adjustable means in the input circuit for zero voltage across the gain adjustment.

6. An amplifier as in claim 5, wherein the adjustable means is a third biasing source.

7. An amplifier circuit for measuring signals with built-in means for drift compensation, comprising:
    an amplifier having an input circuit, a feedback circuit, an an output circuit, the input circuit including first adjustable means for varying the input signal as effective in the amplifier, the feedback circuit including second adjustable resistance means connected to determine the gain of the amplifier circuit;
    first circuit means connected to be responsive to zero or non-zero voltage across the second adjustable resistance means and operating the first adjustable means so that for a first particular measuring signal the second, adjustable resistance means has dynamically established zero voltage across so that the output is independent from the adjustment of the second adjustable means; a source of reference voltage; and second circuit means connected to the output circuit and to the source of reference voltage and operating the second adjustable means for normal operation so that the amplifier output has a particular value in relation to the reference voltage for a second particular measuring signal.

8. A drift compensated amplifier for a measuring signal comprising:
    a differential amplifier having a first input connected to receive the measuring signal and a second input connected to receive a reference potential for the measuring signal;
    adjustable voltage source means connected to the second input;
    a gain circuit including an adjustable resistance means connected to the differential amplifier; a comparator connected to the output circuit of the amplifier and further connected to receive said reference potential; and
    control means connected to be operated by the comparator and operating the adjustable source so that for a particular measuring signal zero volts are established across the adjustable resistance means and the amplifier provides an output equal to the voltage of said biasing source.

9. A drift compensated amplifier comprising a first differential amplifier connected to receive the measuring signal and having an input circuit which includes a first adjustable bias;
    a second differential amplifier with adjustable gain, having one input connected to receive the output of the first differential amplifier, the second differential amplifier having an output circuit;
    a second bias connected to the other input of the second differential amplifier;
    first circuit means connected to the output circuit of the second amplifier and operating the first adjustable bias so that for a first particular measuring signal the output of the second differential amplifier is determined exclusively by the second bias while the gain circuit has zero volts so that the output of the second differential amplifier is independent from the adjusted gain; and second circuit means connected to the output circuit of the second amplifier and operating the gain so that for a second particular measuring signal the second differential amplifier has a second particular output.

10. An amplifier as in claim 9, wherein the output circuit includes a third differential amplifier having one input connected to receive an output of the second differential amplifier and a second input to receive the second bias.

11. An amplifier as in claim 9, wherein the first and second circuit means each include a comparator and a drive means connected to the comparator, the comparator of the first circuit means being connected between the output circuit and the second bias, the drive means of the first circuit means driving said first adjustable bias; and a reference source connected to one input of the comparator of the second circuit means, the other input of the latter comparator being also connected to the output circuit, the drive means of the second circuit means driving the adjustable gain.

12. An amplifier circuit as in claim 7, wherein the first circuit means includes a second source of reference voltage and a comparator connected to the second source and to the output circuit, the comparator providing zero output for zero voltage across the adjustable resistance means, the first circuit means including drive means connected to be responsive to the comparator output for operating the first adjustable means.

13. A circuit as in claim 4, wherein the means for generating includes a gas analyzer and different sources of gas to obtain the particular measuring states.

* * * * *